US010455907B2

(12) United States Patent
Fernandes Demetrio et al.

(10) Patent No.: US 10,455,907 B2
(45) Date of Patent: Oct. 29, 2019

(54) BRACELET FOR A TIMEPIECE

(71) Applicants: José Carlos Fernandes Demetrio, Les Emibois (CH); Anita Durand, La Chaux-de-Fonds (CH); Christophe Pierre, Maîche (FR); Vincent Praplan, La Chaux-de-Fonds (CH)

(72) Inventors: José Carlos Fernandes Demetrio, Les Emibois (CH); Anita Durand, La Chaux-de-Fonds (CH); Christophe Pierre, Maîche (FR); Vincent Praplan, La Chaux-de-Fonds (CH)

(73) Assignee: GEOSATIS S.A., Le Noirmont (CH)

( * ) Notice: Subject to any disclaimer, the term of this patent is extended or adjusted under 35 U.S.C. 154(b) by 97 days.

(21) Appl. No.: 15/510,172

(22) PCT Filed: Sep. 9, 2015

(86) PCT No.: PCT/EP2015/070538
§ 371 (c)(1),
(2) Date: Mar. 9, 2017

(87) PCT Pub. No.: WO2016/038058
PCT Pub. Date: Mar. 17, 2016

(65) Prior Publication Data
US 2018/0020786 A1     Jan. 25, 2018

(30) Foreign Application Priority Data

Sep. 12, 2014 (CH) ....................................... 1381/14

(51) Int. Cl.
*A44C 5/24* (2006.01)
*A61B 5/02* (2006.01)
(Continued)

(52) U.S. Cl.
CPC .................. *A44C 5/24* (2013.01); *A44C 5/12* (2013.01); *A61B 5/02* (2013.01); *A61B 5/72* (2013.01);
(Continued)

(58) Field of Classification Search
CPC .... A44C 5/12; A44C 5/24; A61B 5/02; A61B 5/72; A63B 2230/00; G04C 10/00; G04G 17/06; G04G 21/04
See application file for complete search history.

(56) References Cited

U.S. PATENT DOCUMENTS 3,729,923 A * 5/1973 Brigliano ............... G04B 19/30
                                                      362/103
4,947,179 A   8/1990 Ganter et al.
(Continued)

FOREIGN PATENT DOCUMENTS

EP     0867968 A2     9/1998
EP     1491973 A1    12/2004

OTHER PUBLICATIONS

International Search Report dated Apr. 8, 2016, issued in corresponding International Application No. PCT/EP2015/070538, filed Sep. 9, 2015, 6 pages.
(Continued)

*Primary Examiner* — Sisay Yacob
(74) *Attorney, Agent, or Firm* — Christensen O'Connor Johnson Kindness PLLC

(57) ABSTRACT

A bracelet for a timepiece comprising at least a first strap section and a second strap section, each strap section comprising a first end adapted to be joined to a watchcase and a second end joined to a foldable clasp. The foldable clasp is arranged such that it exhibits an unfolded state, in which the
(Continued)

second ends are at a maximum separation, and a folded state, in which the second ends are maintained at a minimum separation.

4 Claims, 8 Drawing Sheets

(51) Int. Cl.
*A61B 5/00* (2006.01)
*A44C 5/12* (2006.01)
*G04C 10/00* (2006.01)
*G04G 17/06* (2006.01)
*G04G 21/04* (2013.01)

(52) U.S. Cl.
CPC ............. *G04C 10/00* (2013.01); *G04G 17/06* (2013.01); *A63B 2230/00* (2013.01); *G04G 21/04* (2013.01)

(56) References Cited

U.S. PATENT DOCUMENTS

| | | | |
|---|---|---|---|
| 5,280,296 A | 1/1994 | Tan et al. | |
| 5,889,737 A * | 3/1999 | Alameh | G04C 10/00 368/204 |
| 2006/0140055 A1 | 6/2006 | Ehrsam et al. | |
| 2006/0217165 A1 | 9/2006 | Hasumi et al. | |
| 2015/0085623 A1* | 3/2015 | Modaragamage | A44C 5/24 368/10 |
| 2015/0346766 A1* | 12/2015 | Justice | G06F 1/163 361/679.03 |
| 2016/0029778 A1* | 2/2016 | Fitzgerald | A45F 5/02 224/272 |

OTHER PUBLICATIONS

Written Opinion of the International Searching Authority dated Apr. 8, 2016, issued in corresponding International Application No. PCT/EP2015/070538, filed Sep. 9, 2015, 8 pages.

\* cited by examiner

BRACELET FOR A TIMEPIECE

TECHNICAL FIELD

The present invention relates to the field of wearable jewelry. More particularly, it relates to a bracelet with wireless connectivity, for attachment to and use with a timepiece.

STATE OF THE ART

Bracelets with wireless connectivity per se are already known, such as the Nike+ FuelBand activity tracker and fitness monitor, which comprises movement sensors and a Bluetooth communication system for communicating with a smartphone or similar. The Garmin VivoFit is a similar device which furthermore incorporates physiological sensors in the form of a heart rate monitor.

Furthermore, smart watches such as the Apple iWatch and the Samsung Galaxy Gear are also known, and are essentially miniature smart phones presented in the form of a wristwatch.

While such connected bracelets and smart phones are highly functional items, they are not satisfactory from the perspective of a high-end consumer, since they are typically made of plastic and have an electronic display. As such, they are not suitable for wear when questions of presentation demand the wearing of a high-end wristwatch and yet the wearer still wishes to benefit from connectability.

In the field of wrist-mounted selective call receivers, document U.S. Pat. No. 5,280,296 discloses such a receiver in which a loop antenna is provided passing through the bracelet of the receiver. In a particular embodiment, the bracelet has a folding clasp. However, this document is extremely schematic and is insufficiently discloses as to how the antenna makes the transition through the clasp, nor how (or if) it deals with the hinges of the clasp. Since such hinges are conventionally constructed of a solid pin passing through a close-fitting tube, it can supposed that the obvious manner to do so would be to bypass the hinges of the clasp entirely by passing the antenna from one section of bracelet or clasp to the next around the hinge on either the outer side or inner side of the bracelet. Such an arrangement would be deeply unsatisfactory for a high-end application, since the antenna would thus be visible to the user upon inspecting the unfolded clasp, either on the inside or outside of the bracelet.

A first object of the present invention is thus to overcome the above-mentioned drawbacks of the prior art, and thereby provide a bracelet with wireless functionality.

The above-mentioned devices furthermore require that the bracelet be removed for recharging the integrated batteries, which typically have an unimpressive capacity and result in the bracelet being relatively thick. Many consumers prefer not to remove their watches for long periods for recharging, and thus a second object of the invention is to overcome this drawback of the prior art.

Furthermore, it is also desirable to incorporate a silent alarm into such a connected bracelet, so as to alert authorities that a wearer is threatened or undergoing an acute health crisis such as a heart attack or stroke. As such, a third aspect of the invention is to integrate an easily-actuated alarm switch into such a bracelet, preferably a silent alarm switch.

A fourth aspect of the invention relates to a particular arrangement of electronic components in a strap section.

DISCLOSURE OF THE INVENTION

More precisely, said first aspect of the invention relates to a bracelet for a timepiece, the bracelet comprising at least a first strap section and a second strap section, each strap section comprising a first end adapted to be joined to a watchcase and a second end joined to a foldable clasp of any convenient type, the clasp being arranged such that it exhibits an unfolded state, in which said second ends are at a maximum separation, and a folded state, in which said second ends are maintained at a minimum separation, the first strap section comprising at least one first electrical component and the second strap section comprising at least one second electrical component.

According to the first aspect of the invention, the first electrical component is permanently electrically connected to the second electrical component by means of at least one electrical wire passing through the foldable clasp, the foldable clasp comprising at least a first clasp section and a second clasp section joined by a first hinge, the electrical wire passing through a passageway provided through each of the first clasp section, the second clasp section and the first hinge.

As a consequence, both sides of the bracelet can be utilized for electrical components such as antennae, batteries, communication transponders such as Bluetooth transponders, processing units, physiological sensors, movement/acceleration sensors, and so on, since electrical components in each side of the bracelet can be connected and integrated without having to pass through the watch, which can thus be of conventional design, e.g. fully mechanical, without any particular adaptation for connectivity or electronics. Furthermore, the electrical wire is entirely hidden from view, and protected from environmental influences such as water, sweat and so on.

Advantageously, the foldable clasp also comprises a third clasp section joined to the first clasp section by a second hinge, the electrical also passing through a passageway provided through each of the third clasp section, and the second hinge.

Advantageously, the first clasp section is disposed between the second clasp section and the third clasp section, each of the second clasp section and the third clasp section being arranged so as to be contained within the first clasp section when the clasp is in its folded state. The clasp is thus as slim as possible in its folded state, so as to encumber the wearer as little as possible.

Advantageously, the passageway comprises a first groove formed between two adjacently-disposed clasp section sub elements which together form one of the clasp sections.

Advantageously, the passageway comprises a second groove provided through at least one clasp section, e.g. the first clasp section, in a lateral wall thereof, the groove being closed by a cover plate.

Advantageously, each hinge comprises at least one hollow tube, said passageway passing through at least one hollow tube. The bore of this hollow tube permits the electrical wire to pass through the hinge.

Advantageously, the electrical wire forms a loop in at least one of the hinges, which reduces the stresses on the wire during folding and unfolding of the clasp, reducing the risk of fatigue failure of the wire.

Advantageously, the tube comprises a circumferential groove arranged towards each end of the tube, the hinge being secured by pins each passing through one of said clasp sub elements and tangentially through one of said grooves. The hinge is thus secure, and the tube is axially positioned by the pins while permitting passage of the electrical wire.

Advantageously, the electrical components comprise a communication transponder (such as a Bluetooth transponder), an antenna in operative connection with said communication transponder, and a processing unit in operative connection with the communication transponder, and wherein the bracelet further comprises a transducer for measuring at least one physiological property in operative connection with the communication transponder. This physiological property can be one or more of:
- heart rate;
- pulse;
- blood oxygenation;
- blood glucose;
- skin temperature;
- presence of a foreign substance such as alcohol, pharmaceuticals or drugs.

As such, the bracelet of the invention presents all the functionality of prior art connected bracelets yet can be worn with a conventional watch.

Advantageously, the bracelet further comprises a switch in operative connection with the processing unit, said switch comprising a rotor rotatable between a first angular position in which the rotor protrudes above a surface of the bracelet and a second angular position in which the rotor is flush with or sunk with respect to the bracelet, and wherein the state of the switch is determined by the angular position of the rotor. An easily-actuated switch integrated into the bracelet is thus proposed, which can be used for activating an emergency signal.

Advantageously, the switch comprises a reed switch mounted in the interior of the bracelet, and wherein the rotor comprises at least one magnet arranged close the reed switch in one of said angular positions and to open the reed switch in the other of said angular positions. The switch is thus non-contact, and does not comprise any exposed electrical parts, rendering it waterproof.

Advantageously, the bracelet comprises a magnetic détente mechanism adapted to maintain the rotor in the first angular position against unintentional rotation thereof. Further advantageously, the reed switch is a polarised reed switch comprising at least one reed switch magnet, wherein the magnetic détente mechanism incorporates the reed switch magnet and the at least one magnet comprised by the rotor. The operation of the rotor is therefore silent, and the switch and rotor require a minimum number of components in their construction.

Advantageously, the axis of rotation of the rotor is parallel to the longitudinal axis of the bracelet.

Advantageously, the bracelet further comprises at least one battery housing adapted to receive a battery, which may be fixed or removable, the battery housing being situated at said second end of at least one of said strap sections. Further advantageously, each of the strap sections may comprise a battery housing situated at the second end of each strap section. The one or more batteries are thus placed in a convenient position where they does not encumber the wearer, and can be of a greater capacity, and thus size, than if they were integrated into a strap section. Furthermore, space is liberated in the strap sections for electronic components, and the strap sections can be kept as thin as possible.

The battery can either be removable by the user, or not. Removable batteries present the advantage of permitting the user to replace rapidly run-down batteries with full batteries, minimizing the time the bracelet needs to be removed from the wearer's wrist.

Advantageously, the battery housing comprises guiding means adapted to align and support a removable battery, a retaining mechanism for retaining the removable battery in the housing, and an electrical interface arranged to connect the battery to said electrical component. This electrical interface can comprise a friction mechanism or détente mechanism constituting the retaining mechanism.

Advantageously, the bracelet is arranged such that, when the clasp is in its unfolded state, the removable batteries can be removed from their respective housings, and such that, when the clasp is in its folded state, the battery housings are superposed to the clasp such that said removable batteries are blocked in their respective housings and cannot be removed. A further safety against undesired or accidental removal of the batteries is thus attained.

Advantageously, the first end of at least one of the first strap section and the second strap section is adjustable in length. The bracelet can thus be adjusted without requiring the clasp to be adjustable, thereby simplifying the passage of the wire through this latter. To achieve this, for example, the first end of one or more strap sections comprises a number of discrete links which can be added or removed, which results in a particularly simple construction.

The second aspect of the invention relates to a bracelet for a timepiece, the bracelet comprising at least a first strap section and a second strap section, each strap section comprising a first end adapted to be joined to a watchcase and a second end joined to a foldable clasp, the clasp being arranged such that it exhibits an unfolded state, in which said second ends are at a maximum separation, and a folded state, in which said second ends are maintained at a minimum separation, at least one of the first strap section and the second strap section comprising at least one electrical component.

According to the second aspect of the invention, the bracelet further comprises at least one battery housing adapted to receive a battery, which may be fixed or removable, the battery housing being situated at said second end of at least one of said strap sections. The one or more batteries are thus placed in a convenient position where they does not encumber the wearer, and can be of a greater capacity, and thus size, than if they were integrated into a strap section, without unduly inconveniencing the wearer. Furthermore, space is liberated in the strap sections for electronic components, and the strap sections can be kept as thin as possible.

Additionally, the bracelet may comprise a battery housing situated at said second end of each of said strap sections.

Advantageously, the battery housing comprises guiding means adapted to align and support a removable battery, a retaining mechanism for retaining said removable battery in the housing, and an electrical interface arranged to connect the battery to the electrical component.

Advantageously, the electrical interface comprises a détente mechanism constituting the retaining mechanism. No separate détente mechanism is required, reducing the number of pieces required.

Advantageously, the bracelet is arranged such that, when the clasp is in its unfolded state, said removable batteries can be removed from their respective housings, and such that, when the clasp is in its folded state, the battery housings are superposed to the clasp such that said removable batteries are blocked in their respective housings and cannot be removed. A further safety against undesired or accidental removal of the batteries is thus attained.

The third aspect of the invention relates to a bracelet for a timepiece, the bracelet comprising at least one strap section in which is situated electronics comprising a communication transponder, an antenna in operative connection with said antenna, and a processing unit in operative connection with the communication transponder.

According to this aspect of the invention, the bracelet further comprises a switch in operative connection with the processing unit, said switch comprising a rotor rotatable between a first angular position in which the rotor protrudes above a surface of the bracelet and a second angular position in which the rotor is flush with or sunk with respect to the bracelet, and wherein the state of the switch is determined by the angular position of the rotor. An easily-actuated switch integrated into the bracelet is thus proposed, which can be used for activating an emergency signal.

Advantageously, the switch comprises a reed switch mounted in the interior of the bracelet, and wherein the rotor comprises at least one magnet arranged to close the reed switch in one of said angular positions and open the reed switch in the other of said angular positions. The switch is thus non-contact, and does not comprise any exposed electrical parts, rendering it waterproof.

Advantageously, the bracelet comprises a magnetic détente mechanism adapted to maintain the rotor in the first angular position against unintentional rotation thereof. Further advantageously, the reed switch is a polarised reed switch comprising at least one reed switch magnet, wherein the magnetic détente mechanism incorporates the reed switch magnet and the at least one magnet comprised by the rotor. The operation of the rotor is therefore silent, and the switch and rotor require a minimum number of components in their construction.

Alternatively, the switch comprises a hall probe mounted in the interior of the bracelet, and wherein the rotor comprises at least one magnet arranged to interact with said Hall probe in at least one of said angular positions, i.e. such that the hall probe detects either presence or absence of a magnetic field from the magnet, or a reverse in polarity in the case of a pair of oppositely-mounted and oppositely-polarised magnets.

Advantageously, the axis of rotation of the rotor is parallel to the longitudinal axis of the bracelet.

Advantageously, the bracelet comprises battery housing at an end of said strap section, the rotor being attached to a wall of said battery housing.

The fourth aspect of the invention relates to a strap section for a bracelet, particularly a bracelet as defined above. This strap section comprises:
 a support frame comprising frame members defining interstices between said frame members;
 at least two electronic components, which may be of any type such as those discussed above, each electronic component being at least partially situated in a respective interstice; and
 a flexible printed circuit board situated adjacent to a side of the support frame and extending substantially parallel thereto in a longitudinal direction, the flexible printed circuit board being electrically connected to said electronic components and comprising electrical contacts arranged to be connected to a further device, this further device being in particular but not limited to the battery housing as defined above, or even to a watch case.

In consequence, a particularly strong and compact construction of the strap section is proposed, in which the support frame protects the electronic components.

Advantageously, the strap section further comprises an outer sheath surrounding at least the support frame and at least part of the electronic components, the electrical contacts being accessible from outside the outer sheath. This outer sheath is advantageously overmoulded over at least the support frame, e.g. in the case of a rubber sheath, or formed as half-shells attached together, in the case of a leather or other non-mouldable material.

Advantageously, the support frame comprises at least two longitudinal support frame members and at least three transverse frame members which define the said interstices. The longitudinal members are advantageously substantially at right-angles to the transverse members.

Advantageously, the support frame is adapted such that, when the strap section is bent in a direction away from the flexible printed circuit board, the electrical components abut against adjacent transverse frame members (61b). As a result, flexion of the strap section in this direction is limited, so as to protect the electronic components and the flexible printed circuit board from damage due to over-flexing the strap section in this direction.

Advantageously, the transverse frame members extend out of a plane defined by the longitudinal frame members in a direction opposite to the flexible printed circuit board.

Advantageously, the flexible printed circuit board is arranged adjacent to a side of the support frame intended to be facing the wrist of a wearer. Thus, the flexible printed circuit board is protected from damage by being situated on the inside bracelet, away from risk of being impacted by a foreign object.

Advantageously, the electrical components comprise a communication transponder, an antenna in operative connection with said communication transponder, and a processing unit in operative connection with the communication transponder, and/or a transducer for measuring at least one physiological property in operative connection with the communication transponder. Said physiological property may be at least one of: heart rate; pulse; blood oxygenation; blood glucose; skin temperature; presence of a foreign substance such as alcohol, pharmaceuticals or drugs.

BRIEF DESCRIPTION OF THE DRAWINGS

Further details of the invention are described in the following description, in reference to the annexed figures, in which.

EMBODIMENTS OF THE INVENTION

Figure 1:
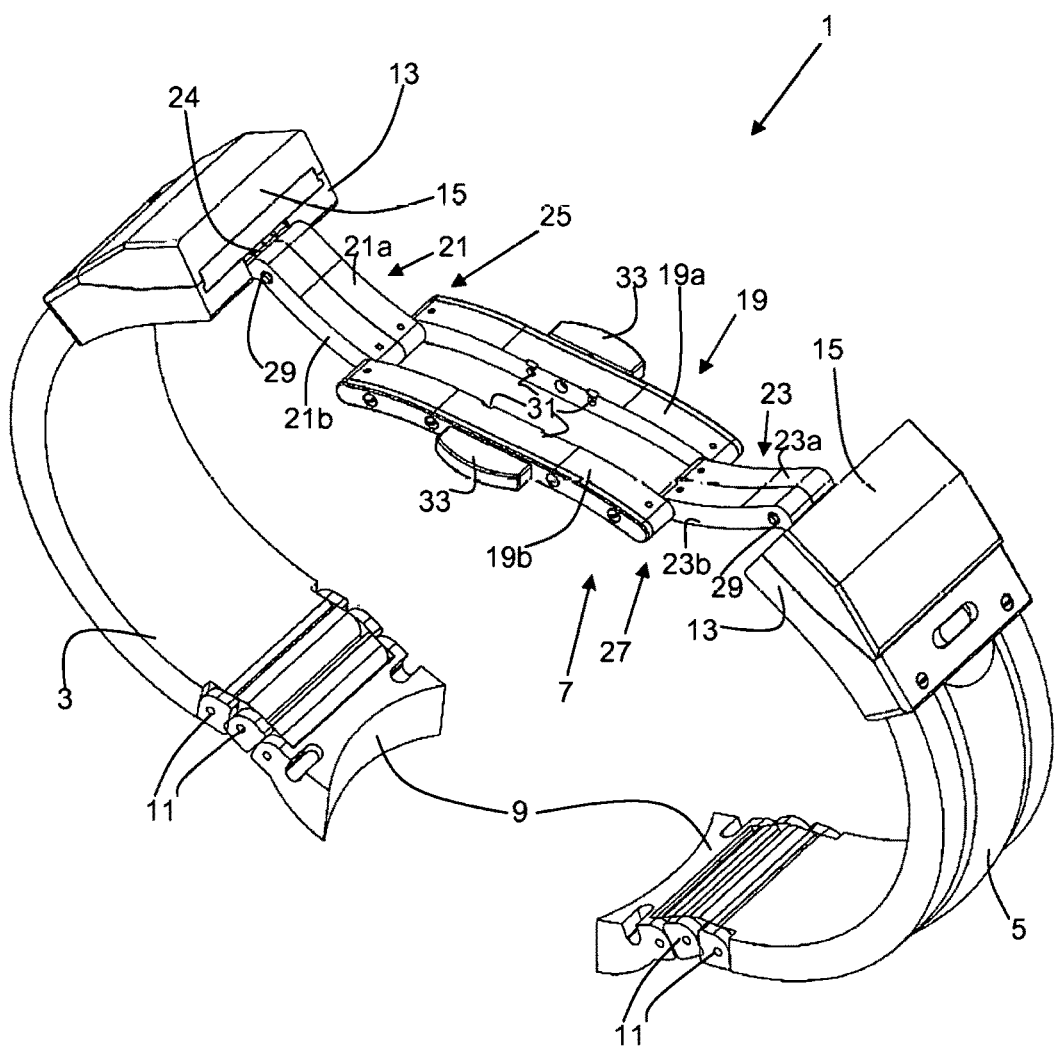
FIG. 1 is a schematic perspective view of a bracelet according to the invention, in which the clasp is open.
Figure 2:
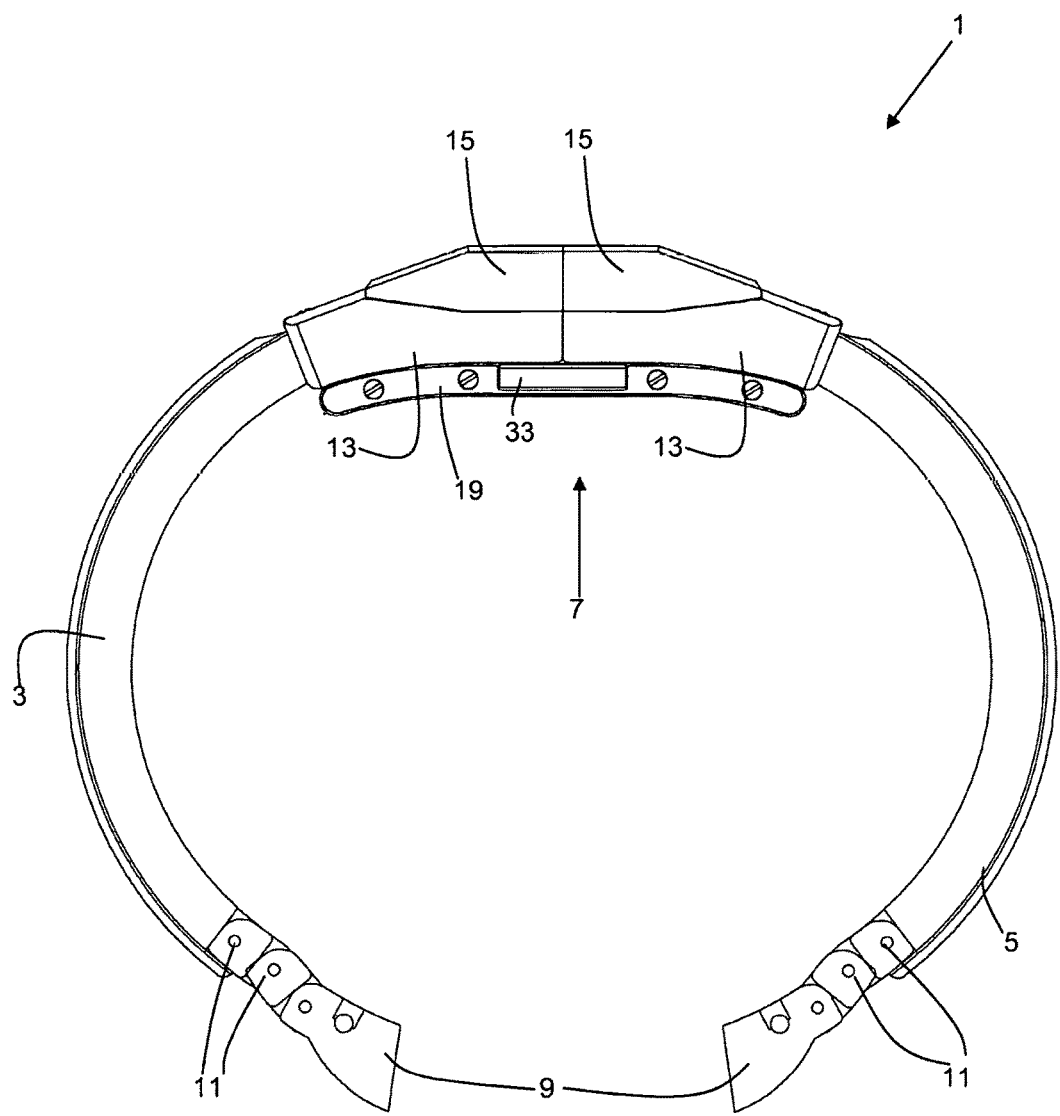
FIG. 2 is a schematic perspective side view of the bracelet of FIG. 1, the clasp being closed.

FIG. 1 illustrates a bracelet 1 according to the invention, with its clasp 7 in an unfolded state, and FIG. 2 illustrates the bracelet 1 with its clasp 7 in a folded state.

Bracelet 1 comprises a first strap section 3, and a second strap section 5. At a first, end of each strap section 3, 5 is provided a watchcase interface piece 9, formed so as to be attachable to a particular watchcase by means of the conventional bar or by any other convenient means. At a second, opposite end of each strap section 3, 5, the strap sections 3, 5 are joined together by a folding clasp 7.

Each interface piece 9 is attached by a number of intermediate links 11 chosen such that the bracelet has the correct circumference for the wearer. Alternatively, an adjustable interface piece 9 or adjustable intermediate links 11 can be used to provide easier adjustment of the bracelet length.

At the second end of each strap section is furthermore provided a battery housing 13 containing a fixed or removable battery 15, which in the present example is removable. In the folded state of the clasp 7, as visible in FIG. 2, the two batteries 15 are situated directly adjacent to each other, and cover the clasp 7. Each battery housing 13 is attached to the remainder of the corresponding strap section 3, 5 by means of screws 14 which pass through corresponding holes in the remainder of the strap section, as is generally known and need not be described further. By situating the batteries in superposition to the clasp 7 in the manner illustrated, larger batteries with higher capacity can be used than in the case of integrated batteries, without unduly affecting the comfort of the wearer.

Figure 4:
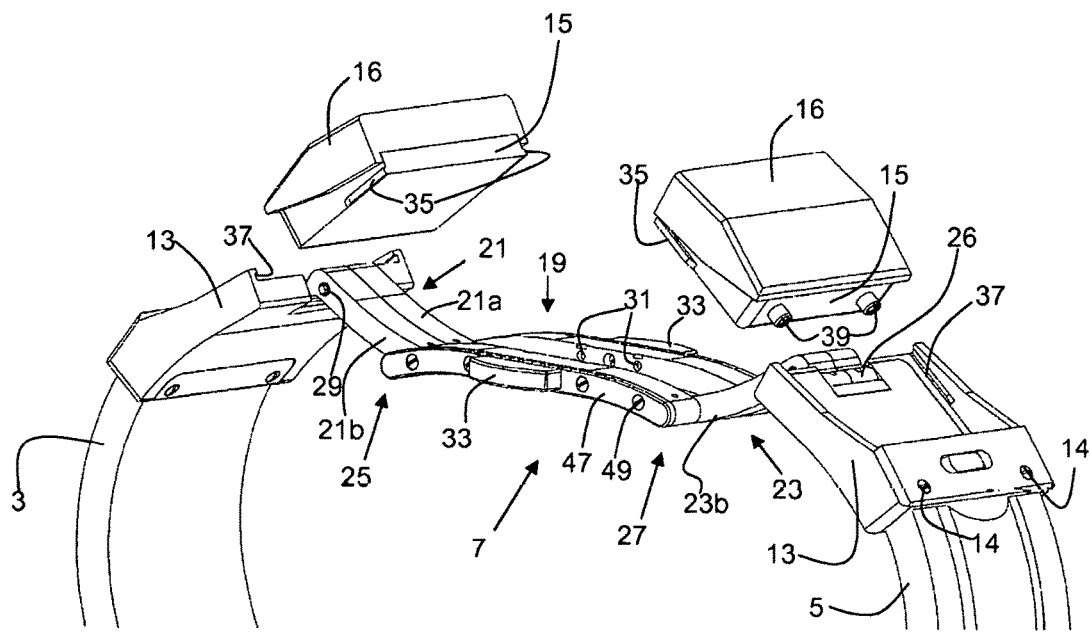
FIG. 4 is a schematic perspective view of the bracelet of FIG. 1, the removable batteries being in position for insertion.
Figure 5:
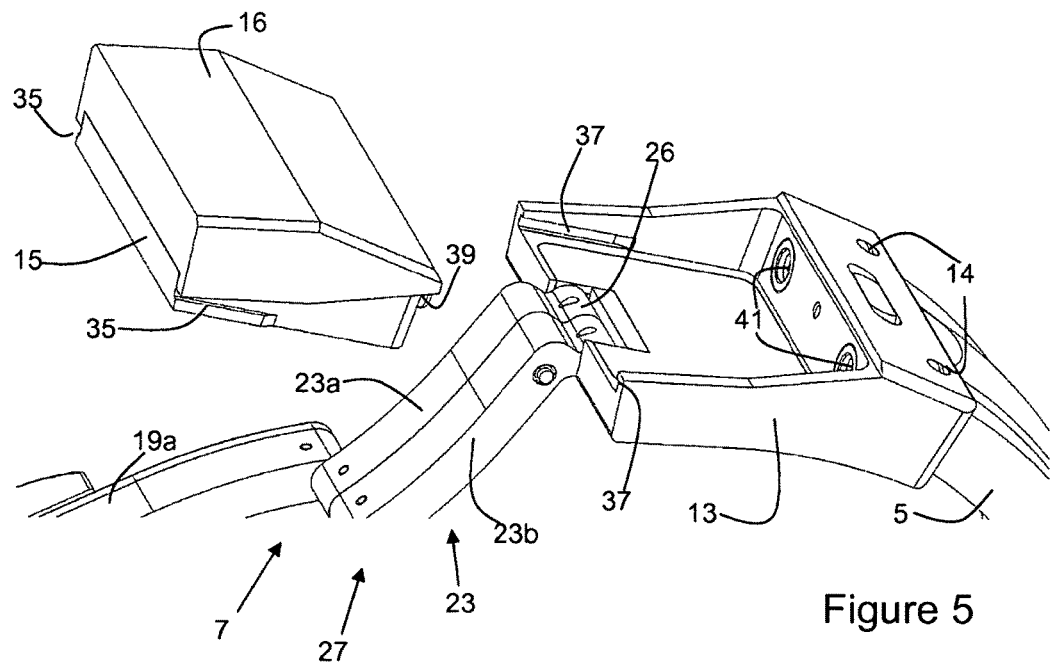
FIG. 5 is a detail view of a battery housing from the reverse angle of FIG. 4.
Figure 6:
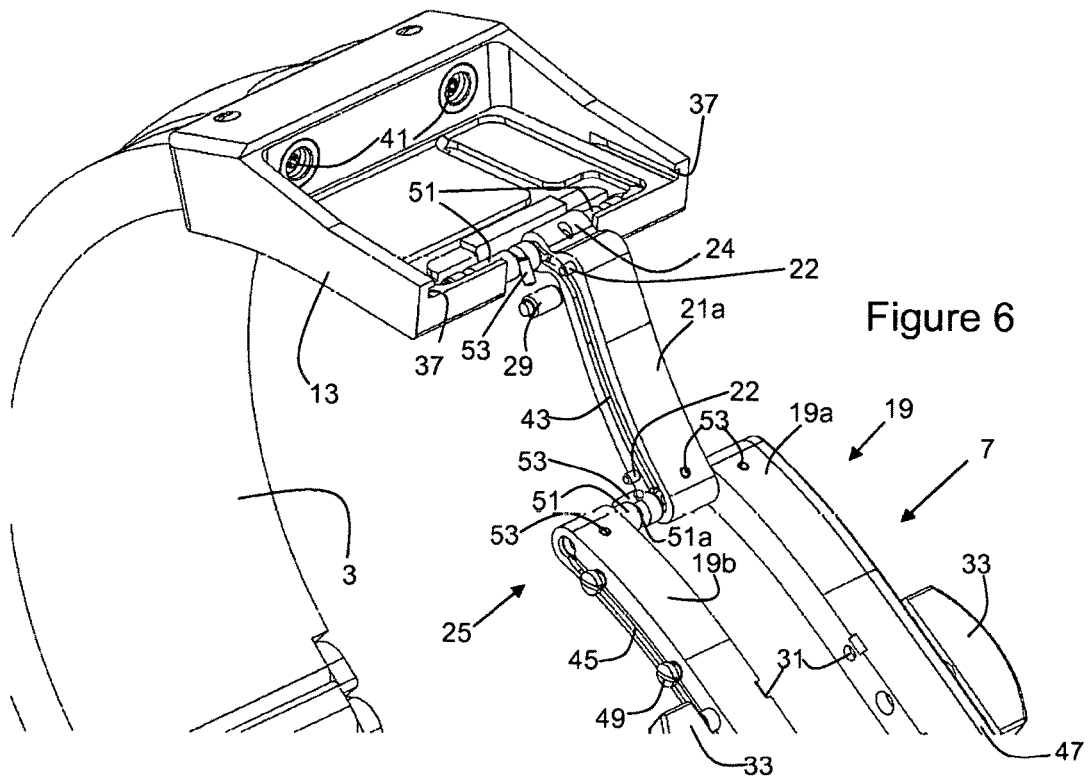
FIG. 6 is a detail view of an empty battery housing and several clasp sections, several parts having been removed.
Figure 7:
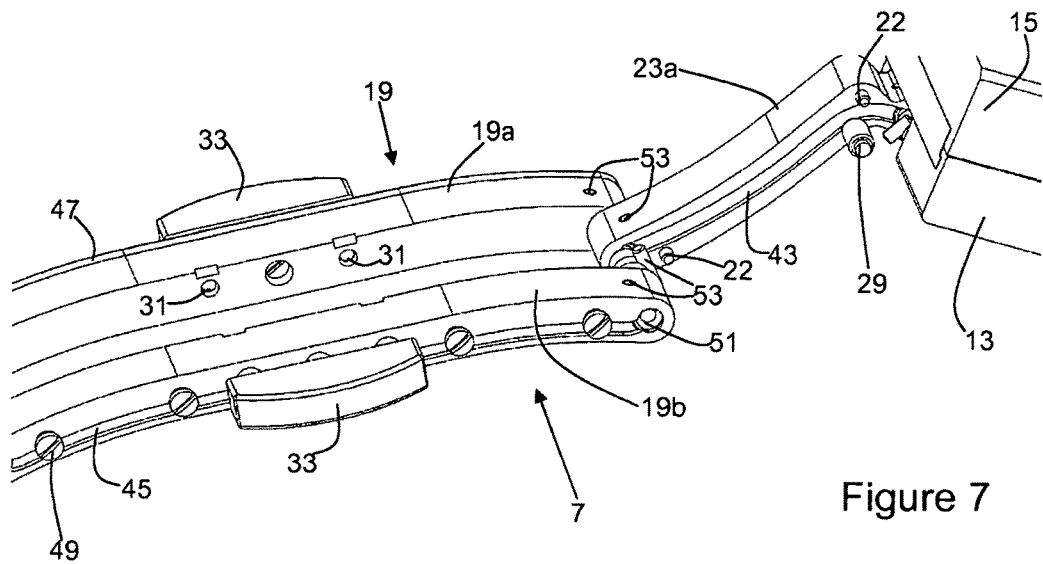
FIG. 7 is a detail view of several clasp sections, several parts having been removed.

As can be seen in FIGS. 4-6, in the illustrated embodiment, each battery 15 is provided with a cover 16 which may be decorated and/or finished to a high standard. Furthermore, each battery 15 and each battery housing 13 comprises guiding means, in particular a pair of rails 35 protruding from the battery 15 and extending parallel to an insertion direction of the battery into its corresponding housing 13, and a pair of longitudinal grooves 37 provided on either side of the battery 15, sized and shaped to cooperate with the rails 35. Naturally, the inverse arrangement of rails and grooves is of course possible, as is a hybrid arrangement in which each of the housing 13 and battery 15 each comprise a rail and a groove. Batteries 15 can therefore be removed when discharged and immediately replaced with a fully charged battery 15, to avoid that the wearer needs to remove the bracelet 1 for a significant length of time for charging. However, it is not excluded that recharging can also take place by wireless recharging or by a wired recharging connection, at least one of which is obligatory in the case that batteries 15 are fixed and non-removable.

In order to electrically connect the batteries 15 with the electronics 17 (see below) comprising at least one electronic component (not individually illustrated) provided in each strap section 3, 5 of the bracelet 1, electrical contacts 39, 41 provided respectively on each of the batteries 15 and in an end wall of each housing 13, which are connected with the electronics 17. In order to retain the batteries 15 in their corresponding housing 13, the electrical contacts 39, 41 are shaped so as to form a retention mechanism such that the batteries 15 are retained within their housings 13 even when the clasp 7 is opened. This may be by simple friction, or by a détente mechanism formed by the electrical contacts 39, 41. Alternatively, a separate retention mechanism may be provided, or the batteries 15 may simply be retained by friction between the battery 15 and its housing 13, particularly at the level of the interaction between the rails 35 and the grooves 37.

Figure 3:
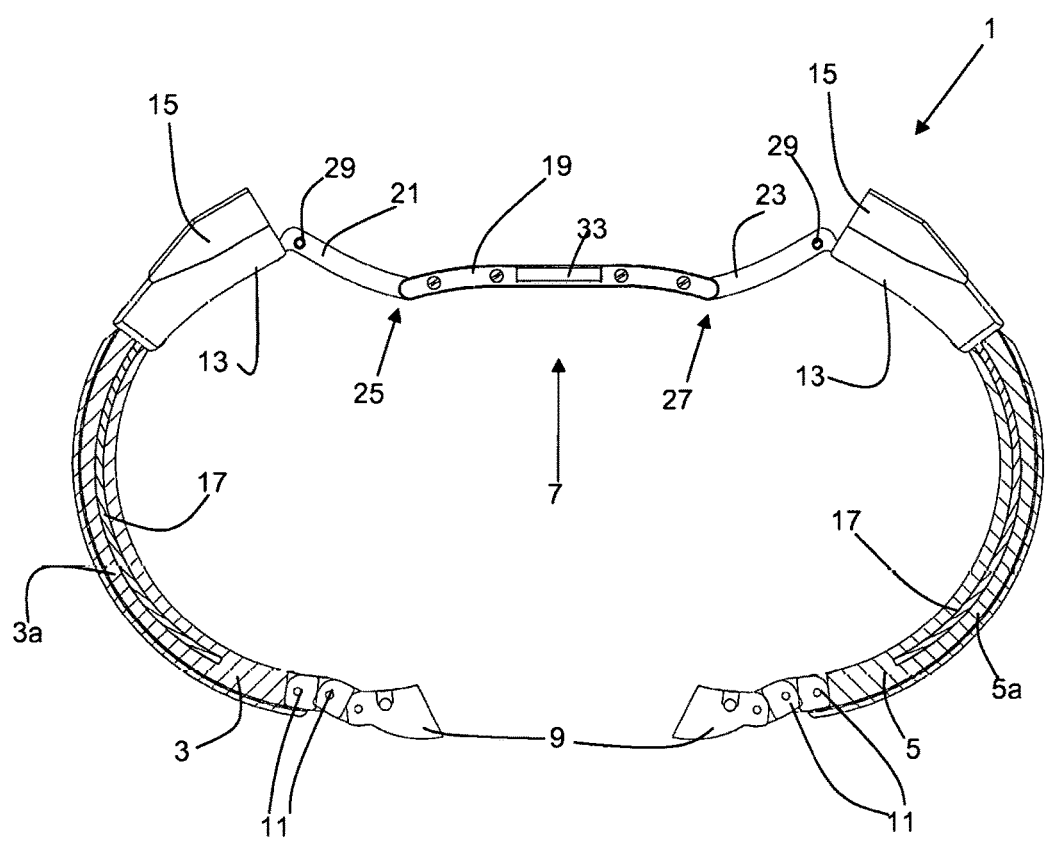
FIG. 3 is a schematic partially cut-away side view of the bracelet of FIG. 1, the clasp being open.

As can be seen in the cross-sectional view of FIG. 3, each strap section 3, 5 of the bracelet 1 further comprises electronics 17, represented here schematically as being situated inside the outer sheath 3a, 5a of the strap section 3, 5. These electronics 17 may comprise a wireless communication system with associated antenna such as a Bluetooth or other convenient system, a GPS transponder, a memory, a processing unit, motion sensors, physiological sensors such as a heart rate sensor, a blood oximetry sensor, a skin temperature sensor, a perspiration sensor, a chemical sensor for detecting a foreign substance such as (but not limited to) alcohol, pharmaceuticals or drugs, or so on. Measurements taken by the sensors can be transmitted via the wireless communication system to an external device such as a smartphone, tablet computer or other computer system either in real-time, or may be stored in a memory provided in one or both of the strap sections 3, 5 for later wireless transfer to such an external device.

Strap sections 3, 5 are constructed of any convenient material, such as leather, plastic, rubber, woven fabrics, metal, and so on. Any sensors requiring skin contact (not illustrated) emerge on the inside surface of the corresponding strap section 3, 5 such that they are placed in contact with the wearer's skin.

Since the bracelet 1 according to the invention is intended to be used with a conventional, "dumb" watch (not illustrated), electrical connection between the electronics 17 provided in each strap section 3, 5 is not possible via the watch. As such, the electrical connection wires 55 (not illustrated in FIGS. 1-7) must pass via clasp 7.

In the embodiment illustrated, clasp 7 is a form of butterfly clasp. However, the same principle as described hereafter applies equally to other types of clasp 7 including but not limited to a trifold (Z-shaped) clasp, a single-fold clasp, and so on.

In the illustrated embodiment, clasp 7 comprises a first clasp section 19 constructed as a hollow frame. This frame is formed of a pair of longitudinal sub elements separated by first and second hinges 25, 27 as will be described in more detail below. Clasp 7 further comprises a second clasp section 21 connected via a third hinge 24 to the corresponding battery housing 13 and via said first hinge 25 to the longitudinal sub elements of first clasp section 19 at a first end of this latter, and is adapted so as to be able to fold inside and be flush with first clasp section 19.

In addition, clasp 7 also comprises a third clasp section 23 likewise arranged in mirror image to the second clasp section 21 and likewise connected to the first clasp section 19 via said second hinge 27 provided at a second end of the first clasp section 19. Third clasp section 23 is likewise connected to the corresponding battery housing 13 by a fourth hinge 26. To retain the clasp in its closed position, second and third clasp sections 21, 23 are provided with outward-facing spring-loaded pins 29, which interface with corresponding sockets 31 in the generally understood manner. Furthermore, pushbuttons 33 are provided to release the spring-loaded pins 29. Alternatively, pushbuttons 33 can be deleted, sockets 31 being formed such that they form a detente mechanism together with the pins 29, the clasp 7 being released simply by pulling it open against a retention force provided by the detente mechanism. Naturally, other forms of retention mechanisms are possible.

For the passage of the electrical connection wires 55 through the clasp 7, passageways are provided through the clasp so as to house the wires 55. As can be seen from FIGS. 6 and 7, the passageways provided through each clasp section 19, 21, 23 are formed as closed grooves forming channels which are invisible from the exterior. To better illustrate these grooves, in FIGS. 6 and 7 one clasp subsection 21b, 23b of each of second and third clasp sections 21, 23 has been removed, as has a cover plate 47 of a clasp subsection 19b of first clasp section 19.

In the case of second clasp section 21 and third clasp section 23, each of these clasp sections is formed by a pair of mirror-image clasp sub elements 21a, 21b, 23a, 23b respectively, assembled with the assistance of lateral alignment pins 22 which enter into corresponding holes as is generally known. On an inward-facing lateral face of each clasp sub element 21a, 21b, 23a, 23b is provided a first groove 43 extending from hinge bore to hinge bore, which, when each clasp section 21, 23 is mounted, together form a passageway in which one or more electrical wires 55 can be situated. Of course, it is not necessary that each clasp sub element 21a, 21b, 23a, 23b comprises a groove, since a sufficiently large groove provided in one or other clasp sub element of each of second clasp section 21 and third clasp section 23 is sufficient.

In the case of first clasp section 19, a second groove 45 is provided on an outer face of each of the longitudinal sub elements 19a, 19b, which is closed on the lateral side by a cover plate 47 held in place by screws or bolts 49. Please note that in the views of FIGS. 6 and 7, cover plate 47 situated on longitudinal sub element 19b has been removed so as to show groove 45. Groove 45 passes underneath (considered in the orientation of the figures) pushbutton 33 and the associated clasp release mechanism. Naturally, only one groove 45 and corresponding cover plate 47 need be provided in the case of very fine wires or a single wire.

In order that the passageway for the electrical wire 55 can pass through each of the hinges 24, 25, 26, 27, each hinge is constructed using a pair of tubes 51, each tube 51 connecting a sub element of each clasp section to the adjacent sub element of the following clasp section or to the adjacent battery housing 13, as appropriate. These tubes 51 are arranged in pairs, extending outwards from the centreline of each hinge 24, 25, 26, 27. To retain each tube 51 in position while permitting rotation of each hinge 24, 25, 26, 27, the tubes 51 are provided with circumferential grooves 51a (see in particular FIG. 8) situated towards each extremity of the tube 51, each groove being located within a corresponding bore provided in each clasp section subelement. A pin 53 passes through a transverse hole in the corresponding clasp section subelement such that the pin 53 passes tangentially through the corresponding groove 51a, thereby retaining the tube 51 in its axial position. Alternatively, bolts or screws could be used.

Each open end of the tube 51 terminates in a small cavity forming part of the passageway sufficient for the wire 55 passing therethrough can make the turn from the bore 51b of the tube 51 to the adjacent groove 43, 45. Passageway for the wire 55 is thus formed by the bore 51b through each tube, and grooves 43, 45.

Figure 8:
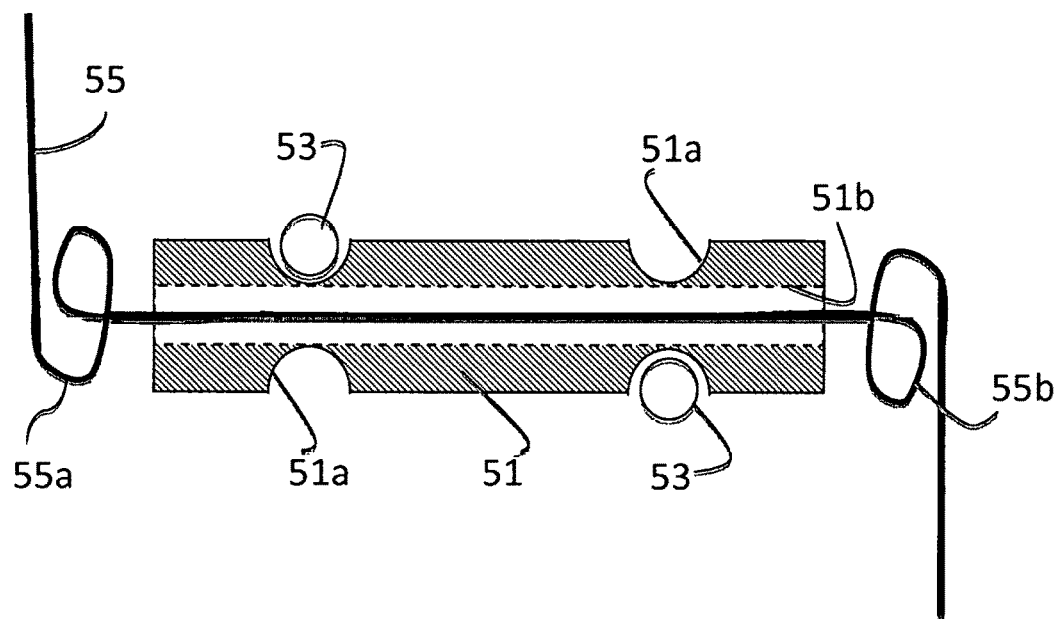
FIG. 8 is a schematic view of the passage of a wire through a tube.

Although the wire 55 can simply make the 90° bend at the transition from each tube 51 to the adjacent groove 43, 45, this can apply significant stress to the wire 55, particularly in the case of repeated folding and unfolding of the clasp 7, with an accompanying risk of fatigue failure of the wire. FIG. 8 illustrates a way to minimise the stress on the wire 55. The vertically-oriented sections of wire 55 illustrated in FIG. 8 represent wire 55 entering and leaving a hinge via a groove 43, 45. In making the turn into the bore 51b of the tube 51, wire 55 is formed into a first loop 55a in a first direction (e.g. clockwise). Wire 55 then passes along the bore 51b, at the other end of which it is formed into a second loop 55b in a second direction (e.g. anticlockwise), preferably opposite to the first direction, before continuing further along the passageway in the subsequent groove 43, 45.

These loops minimise the stress placed on the wire 55 when the clasp 7 is folded and unfolded, reducing the risk of breakage.

Figure 9:
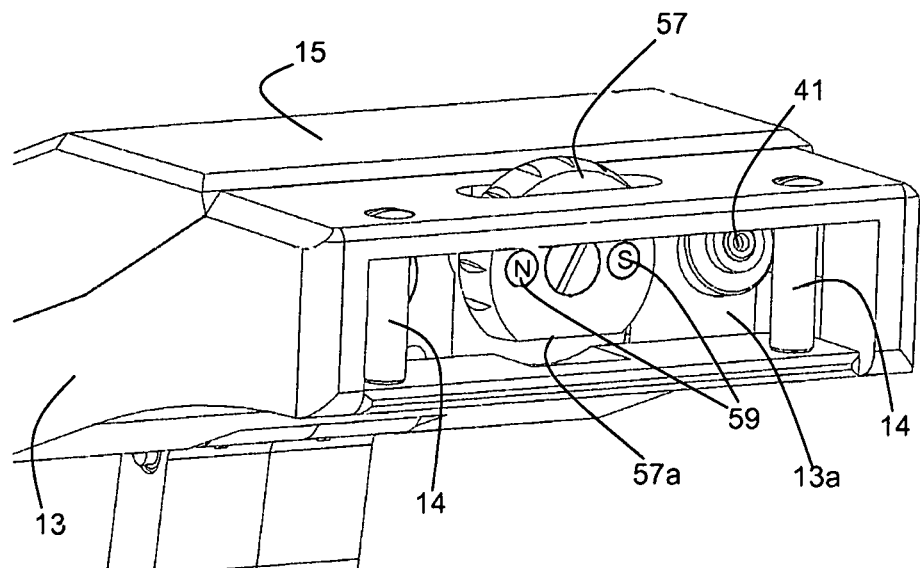
FIGS. 9 and 10 are schematic perspective views of details of a switch provided in the bracelet.
Figure 10:
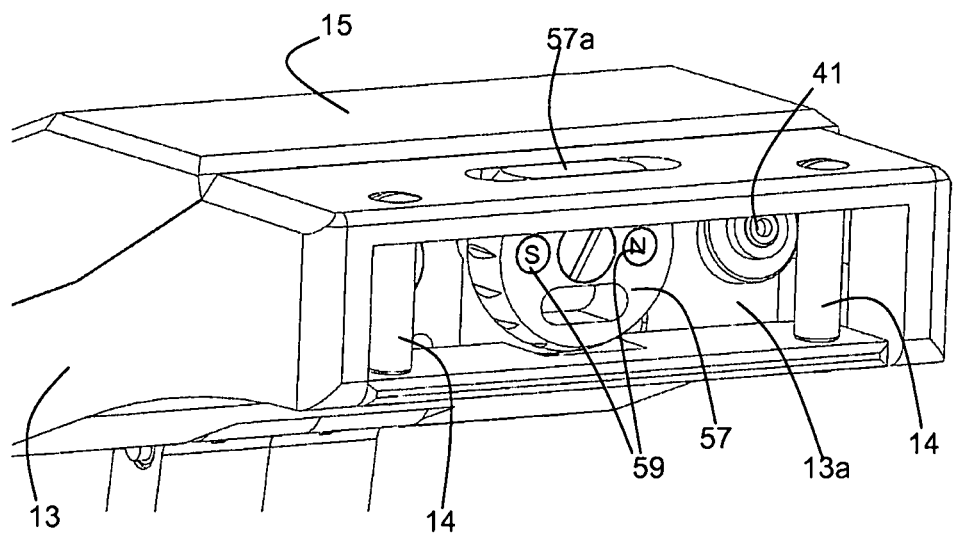

A further aspect of the present invention is represented in FIGS. 9 and 10, in which the remainder of the second strap section 5 has been removed so as to see into the reverse side of a battery housing 13.

As can be seen on FIGS. 9 and 10, the battery housing 13 furthermore comprises a rotor 57, which comprises a flat edge 57a. Rotor 57 is pivoted on the battery housing such that it rotates on an axis perpendicular to the width of the strap section 5 between a position in which it protrudes above a surface of the bracelet 1, in particular an exterior surface of the battery housing 13 (see FIG. 9), and a position in which flat edge 57a is flush with or slightly recessed in respect of this surface (see FIG. 10).

The rotor 57 comprises a pair of magnets 59 of opposite polarisations and situated either side of the axis of rotation of the rotor 57, diametrically opposed to one another. The magnetic field lines emanating from the magnets are oriented at their origin substantially parallel to the axis of rotation of the rotor 57. Behind the rotor 57 (hidden by the rotor 57 and thus not visible) is situated a polarised reed switch arranged to be open when the magnets 59 are in one position (e.g. the position and orientation of FIG. 9) and closed when magnets 59 are in an opposite position (e.g. the position and orientation of FIG. 10). Alternatively, a single magnet 59 can be used in combination with a polarised or non-polarised reed switch. Reed switch may be situated as convenient, and may be encapsulated in the wall of the battery housing 13. This reed switch is electrically connected to electronics 17, in particular a processing unit thereof, contained within one of the strap sections 3, 5. Alternatively, a Hall probe may be used in place of a reed switch. The reed switch or Hall probe may be sited on either side of the end wall 13a of battery housing 13, or even moulded into the end wall 13a.

Rotor 57 and the reed switch thus form an on-off switch which can be actuated by the user by rotating the rotor 57 in either direction until the flat edge 57a is flush with the surface of battery housing 13.

The use of a reed switch, or indeed a Hall probe, has several advantages. Firstly, is permits excellent water-tightness, since it contains no external moving parts or exposed electrical contacts. Secondly, it can operate essentially silently, and thus be used for a silent alarm, alerting authorities e.g. via an integrated mobile telephone or other communication system, or via Bluetooth to another device such as a smartphone which then alerts the authorities silently in response to actuation of the switch by the user, in the case of the wearer being in imminent danger due to being attacked or feeling the onset of acute health problems such as a heart attack or stroke. In addition, due to the placement of the rotor 57 in the bracelet in the manner illustrated, it can easily be actuated by the user even if his hands are restrained. To assist in this end, the rotor 57 itself can also operate silently, and does not require any form of mechanical détente which might emit an audible "click" sound that might alert another person that an alarm has been actuated. By careful arrangement of the polarised reed switch (which contains one or more magnets) or arrangement of further magnets, a contactless détente can be formed between the rotor and the reed switch. This maintains the rotor 57 in the inactivated position (FIG. 9) until deliberate manipulation by the user brings it into its activated position (FIG. 10).

Figure 11:
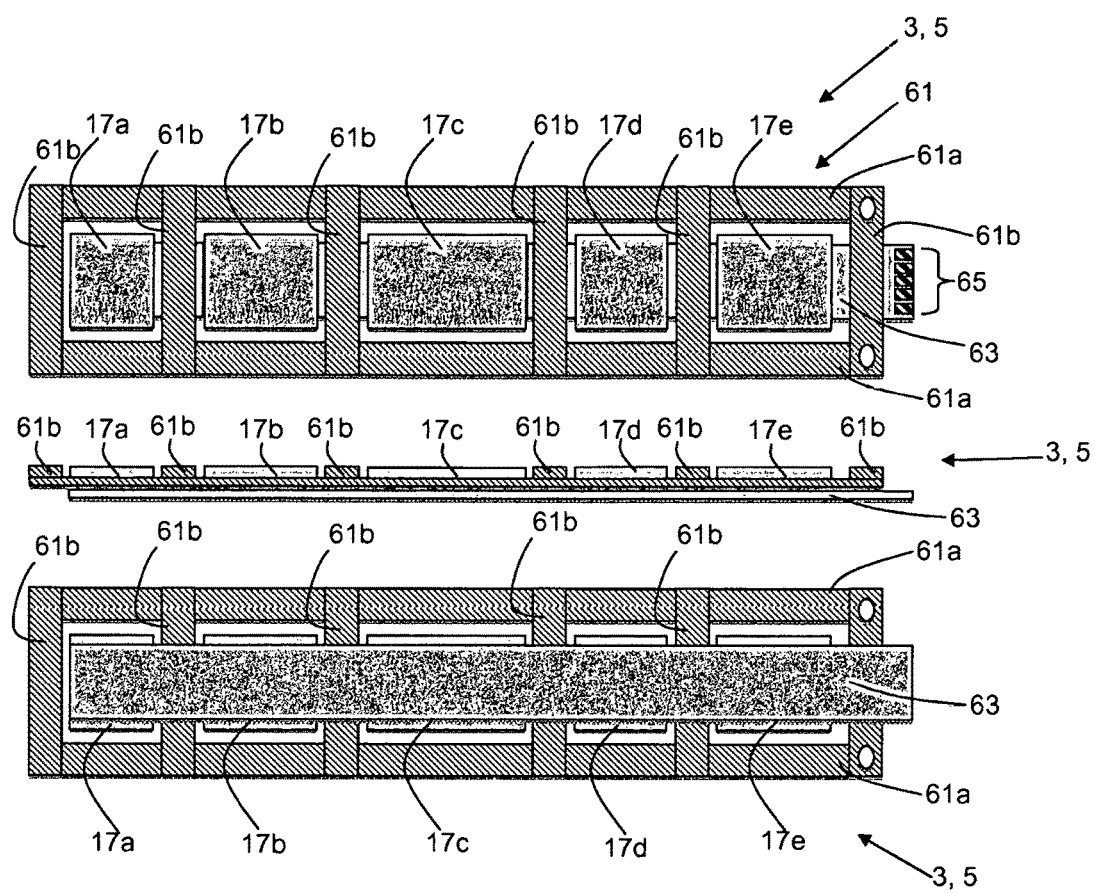
FIG. 11 represents schematic views of an arrangement of electronic components in a strap section.

A yet further aspect of the invention is illustrated in FIG. 11, which illustrates schematically, from top to bottom, a variant of the internal structure of a strap section 3, 5, the outer material forming the sheath 3a, 5a (see FIG. 3) of the strap section 3, 5 having been removed. This sheath 3a, 5a can be either overmoulded over the internal structure (for instance in the case of a rubber sheath) and at least part of the electrical components, or formed as two half-shells (for instance in the case of a leather strap section). Other constructions are of course possible.

In this construction, the strap section 3, 5 comprises a support frame 61, made of for instance metal, fibre (e.g. carbon fibre, aramid, polyester fibre etc.). The support frame 61 comprises two longitudinal frame members 61a extending parallel to the longitudinal axis of the strap section 3, 5 and spaced apart from one another by transverse frame members 61b, thereby forming interstices in which are situated electronic components 17a-17e, forming the electronics 17 of the bracelet, and which comprise elements of any of the above-mentioned types. It is of course not necessary that the frame members 61a, 61b are arranged longitudinally and transversely—they could equally be arranged in a diamond criss-cross pattern, as a ribbon form with circular, oval, triangular, or polygonal interstices, or any other convenient arrangement. Furthermore, the various frame members 61a, 61b can be formed integrally or as separate parts subsequently joined together, may all be arranged in the same plane, in different or overlapping planes, and may have the same or different thicknesses. Furthermore, fixing holes 62 are provided to fix the strap section 3, 5 to the screws 14 of the battery housing 13.

In the illustrated embodiment, the electronic components 17a-17e are thicker than the support frame 61, and thus protrude above and below the plane of the support frame 61. However, this does not have to be the case.

The strap section further comprises a flexible printed circuit board (PCB) 63, which extends in a longitudinal direction on one side of the support frame 61, and serves as an electrical connection for the electronic components 17a-17e. Advantageously, this flexible PCB 63 is arranged on the side of the strap section which will be oriented towards the skin of the wearer, and is thus protected from damage. However, the PCB 63, or a supplemental PCB can be arranged on the side of the strap section 3, 5 which will be worn away from the wearer's skin. Furthermore, it is also possible to integrate electrical connections in or on the members of the support frame 61, either as a flexible PCB or as individual wire connectors.

In order to reduce the risk of damage to the electronic components 17a-17e and to the flexible PCB 63, the dimensions of the transverse frame members 61b and their distance from the adjacent electronic components 17a-17e are chosen so as to limit the flexion of the strap section 3, 5 in the direction away from the flexible PCB 63. In particular, the transverse frame members 61b can extend further in this direction than the longitudinal frame members 61a. In the case of a flexion in this direction, the transverse frame members 61b abut against the electronic components 17a-17e and do not permit any further flexion in the same direction. This furthermore limits the tension to which the flexible PCB 63 is subjected, reducing the risk of damage. This arrangement however permits sufficient flexion in the opposite direction so that the bracelet 1 can conform to a variety of differently-sized wrists.

So as to connect electrical components 17a-17e to the battery housing 13, and also to other electrical components in the adjacent strap section, the end of the flexible PCB 63 is provided with a plurality of electrical contacts 65, which, when assembled, enter into electrical contact with corresponding contacts (not illustrated) in the battery housing 13 in the case of the bracelet as defined above, or in the case of a more conventional bracelet arrangement, with electrical contacts provided in a watch case e.g. of an electric or electronic timepiece. These corresponding electrical contacts can be for instance in the form of a suitably-formed socket.

In the case in which one or more of the electrical components 17a-17e requires contact with the skin of the wearer, such as a heart rate monitor, the corresponding electrical component can pass through the flexible PCB and through the sheath 3a, 5a so as to contact the skin. Alternatively, separate sensors or similar can be built into the sheath 3a, 5a in a position such that they come into contact with the wearer's skin, and are then connected to the corresponding electrical component 17a-17e via wires or via the flexible PCB.

Although the invention has been described in terms of specific embodiments, variations thereto are possible without departing from the scope of the invention as described in the appended claims.

The invention claimed is:

1. A bracelet for a timepiece, the bracelet comprising:
at least a first strap section and a second strap section, each strap section comprising a first end adapted to be joined to a watchcase and a second end joined to a foldable clasp, the foldable clasp being arranged such that it exhibits an unfolded state, in which said second ends are at a maximum separation, and a folded state, in which said second ends are maintained at a minimum separation, the first strap section or the second strap section comprising at least one electrical component,
first and second battery housings each adapted to receive a battery, the first and second battery housings being situated at said second ends of said first strap section and second strap section, respectively.

2. The bracelet according to claim 1, wherein the bracelet is arranged such that, when the foldable clasp is in its unfolded state, said removable batteries can be removed from their respective housings, and such that, when the foldable clasp is in its folded state, the battery housings are superposed to the foldable clasp such that said removable batteries are blocked in their respective housings and cannot be removed.

3. A bracelet for a timepiece, the bracelet comprising:
at least a first strap section and a second strap section, each strap section comprising a first end adapted to be joined to a watchcase and a second end joined to a foldable clasp, the foldable clasp being arranged such that it exhibits an unfolded state, in which said second ends are at a maximum separation, and a folded state, in which said second ends are maintained at a minimum separation, the first strap section or the second strap section comprising at least one electrical component,
at least one battery housing adapted to receive a battery, the at least one battery housing being situated at said second end of at least one of said strap sections, and
wherein said at least one battery housing comprises guiding means adapted to align and support a removable battery, a retaining mechanism for retaining said removable battery in the housing, and an electrical interface arranged to connect the battery to said electrical component.

4. The bracelet according to claim 3, wherein the electrical interface comprises a détente mechanism constituting the retaining mechanism.

\* \* \* \* \*